United States Patent [19]

Salvado et al.

[11] Patent Number: 4,961,346

[45] Date of Patent: Oct. 9, 1990

[54] APPARATUS FOR PERFORMING ULTRASONIC MEASUREMENTS

[75] Inventors: Carlos A. Salvado, Carlsbad; Bruce E. Wade, Del Mar, both of Calif.

[73] Assignee: The Expert System Technologies, Inc., San Diego, Calif.

[21] Appl. No.: 290,810

[22] Filed: Dec. 23, 1988

Related U.S. Application Data

[63] Continuation of Ser. No. 930,121, Nov. 12, 1986, abandoned.

[51] Int. Cl.$^5$ ............................................. G01N 29/00
[52] U.S. Cl. ..................................................... 73/644
[58] Field of Search ................. 73/597, 622, 633, 644; 310/336, 328, 348

[56] References Cited

U.S. PATENT DOCUMENTS

| | | | |
|---|---|---|---|
| 3,019,637 | 2/1962 | Cook et al. | 310/336 |
| 4,165,649 | 8/1979 | Greer, Jr. | 73/644 |
| 4,259,868 | 4/1981 | Rao | 73/597 |
| 4,361,154 | 11/1982 | Prait, Jr. | 73/597 |
| 4,462,082 | 7/1984 | Thiele | 364/571 |
| 4,479,387 | 10/1984 | Wagner et al. | 73/622 |
| 4,481,820 | 11/1984 | Thomann | 73/597 |
| 4,494,408 | 1/1985 | DeLacy | 73/587 |
| 4,494,410 | 1/1985 | Van Bochove et al. | 73/644 |
| 4,499,770 | 2/1985 | Kriz | 73/599 |
| 4,522,068 | 6/1985 | Smith | 73/32 A |
| 4,689,996 | 9/1987 | Huschelrath | 73/643 |

OTHER PUBLICATIONS

Ultrasonic Att. as an indicator of fatigue life of GFE composite, Materials Evaluation, J. H. Williams et al. May 1980.

Primary Examiner—Hezron E. Williams
Assistant Examiner—Louis M. Arana
Attorney, Agent, or Firm—Gregory O. Garmong

[57] ABSTRACT

An apparatus for performing ultrasonic measurements of compliant material specimens includes a pair of facing but spaced apart ultrasonic transducers between which the specimen is placed, and which transmits signals into the specimen and receives signals from the specimen, a structure which presses the transducers against the opposite surfaces of the specimen with a reproducibly controllable force so that the same compressive force may be applied for successive measurements, a gauge that measures the separation of the two transducers, and a controller which drives the transmitting transducer and receives the signals from the receiving transducer. The apparatus permits the determination of comparable ultrasonic properties for different points on one specimen, and the determination of comparable properties of a number of specimens, by making the measurements under identical conditions. The apparatus can be provided in a hand-held form and in a form used for inspections when only one side of the specimen is accessible.

4 Claims, 2 Drawing Sheets

APPARATUS FOR PERFORMING ULTRASONIC MEASUREMENTS

This application is a continuation of application Ser. No. 930,121, filed Nov. 12, 1986 now abandoned.

BACKGROUND OF THE INVENTION

This invention relates to measuring devices for measuring properties of specimens, and, more particularly, to an ultrasonic device for measuring such properties.

Structures are built from materials which are normally selected for their high modulus and strength, and for acceptable collateral properties such as resistance to environmental damage, fatigue resistance and fabricability. For many years, metal alloys were the preferred structural materials for aircraft and spacecraft applications. More recently, composite materials made of bonded mixtures of different components have been developed and refined for use in specific applications. Composite materials can be prepared that have higher elastic modulus and strength per unit weight than metals, and therefore have become of great interest for use in advanced structures.

The properties of composite materials can be varied over wide ranges through control of the properties of the components and the amounts of each component present. Composite materials can be intentionally fabricated to have specified elastic and strength properties in the directions wherein such properties are required, and can even be tailored to have different properties within a single continuous part. The composite materials therefore offer designers the opportunity to greatly improve the performance of structures, but also impose some additional burdens on those who build and maintain the structures. That is, since the composite materials are of such a nature that they can be fabricated with widely varying properties, each composite structure that is built must be carefully monitored to ensure that it is within the limits specified by the designers.

One of the currently most important types of composite materials is fiber composites of graphite, glass or Kevlar fibers in a thermoset or thermoplastic matrix, which are used in advanced aircraft and spacecraft structures as well as commercial applications such as tennis rackets and golf clubs. These composite materials are a mixture of oriented or unoriented fibers in a matrix which binds the reinforcement together and also protects it. It is vital to know accurately the fractions of each of the components present in the material and the amount of moisture present in voids within the material, as large variations in component fractions and too much moisture may lead to otherwise undetectable sources of failure.

Parts made from such fiber composites are usually fabricated by filament winding or by bonding together thin plies of "prepreg", a precursor material made of the reinforcement fibers in an uncured matrix that is available as sheets about 0.004–0.008 inches thick. The prepreg is of interest in itself, as its properties must be evaluated during manufacture and prior to bonding to be certain of its quality. Sheets of the prepreg are stacked together or "laid up" to form thick pieces termed laminates, and these laminates are cured in autoclaves to form semifinished parts.

The local weight fraction of the resin matrix and the reinforcement fibers, and the local presence of moisture should be known for both the prepreg and the cured final part. In the latter case, it is desirable that the moisture content of the composite material be known for the prepreg, upon curing, and also after field service. Moisture can be absorbed into these composite materials during fabrication of the prepreg and the layups, or during service. The moisture is highly damaging to the material, and can lead to premature failure of the part.

At the present time, information about the local weight fraction of reinforcement fibers and matrix can be determined readily only by destructive testing, and information about the moisture content can be determined only by laborious and partially destructive techniques such as desiccation. In the usual commercial procedure for determining weight fractions, a piece of the composite material is cut away from the rest and weighed. The matrix is then chemically or thermally removed, leaving only reinforcement particles. The particles are weighed, and the weight is divided by the total weight of the piece to determine weight fraction. From calibration tables or known transformations, the volume fraction is calculated. The weight fraction of matrix is calculated as one minus the weight fraction for the fiber. Where volume is conserved, the volume fraction of matrix is one minus the volume fraction for the fiber. Measurements of moisture are accomplished by vacuum desiccation of pieces of the composite material, weighing the material before and after desiccation to determine the moisture lost. Both types of measurements cannot be done with a part in service without having the evaluation procedure itself do significant harm to the structure, unless test coupons are built into the part. Even then, the actual local composition and moisture content cannot be evaluated, only inferred from measurements of neighboring areas.

Composite materials are entering more widespread use in applications such as commercial and military aircraft structures for which the fractions of the phases and the moisture content, as well as any microstructural irregularities, must be accurately known both at the time of manufacture and during service. Deviations from specified values can lead to local weaknesses, which in turn might result in failure of the part made of the composite material. An accurate, reliable approach to measuring the characteristics of materials formed of mixtures is required so that the prepreg starting material, the laminates, and the service part can be readily sampled and evaluated.

The preceding discussion has focussed on one specific type of mixture, composite materials. However, the problem of determining the component fractions of a previously formed mixture is found in many other areas, including geology, mineralogy, construction, automotive tire production, and manufacturing. A solution of the problem for mixtures such as composite materials would likely be applicable to, and would provide valuable benefits in, these fields also.

Accordingly, there exists a need for a testing device which permits a determination of the weight fractions of the phases, and the moisture content, in a mixture such as a composite material. The apparatus must permit testing of prepreg and finished parts, without damaging the specimens and in a manner that is economical and consistent with large scale testing. The present inventors have determined that such measurements can be accomplished with ultrasonic apparatus, but have found that the existing types of ultrasonic measurement apparatus cannot make the required measurements and meet the above-stated requirements. The present invention fulfills the need for an ultrasonic apparatus meeting these requirements, and further provides related advantages.

SUMMARY OF THE INVENTION

The present invention provides an apparatus and procedure for performing ultrasonic measurements, such as measurements of velocity and attenuation, on specimens in a reproducible, precise manner that permits accurate determinations of physical properties and also permits comparisons of data taken from different specimens, from different areas of a single specimen, and from the same specimen at different times. The apparatus is operable with compliant materials, whose deformation can interfere with obtaining reproducible measurements. When compliant materials are evaluated, the specimen under study is not contaminated with couplants made of foreign matter, but coupling is achieved in a fully reproducible fashion. When rigid specimens are evaluated, minimal amounts of volatile couplants, or a compliant transducer, may be utilized. The apparatus and procedure can be used for composite prepreg, cured composite, and a wide variety of other types of materials, both in a laboratory environment and also in a factory or even a service environment, with reproducibility and precision maintained throughout the variety of tests.

In accordance with the invention, apparatus for performing ultrasonic measurements on a solid specimen comprises measurement means for introducing a first ultrasonic signal into the specimen and for receiving a second ultrasonic signal from the specimen, compression means for forcing the measurement means against the surface of the specimen with a reproducibly controllable constant compressive force, so that the same compressive force may be applied on successive measurements, and control means for controlling said measurement means.

Coupling of the transducers to the specimen is accomplished by compressing the transducers against the surface with a precise, reproducible force such as, for example, dead-weight loading, spring loading, or controlled loading by a device such as a robotic arm. The extent of coupling is the same for every specimen for which the same compressive force is used. The nature of the coupling can be understood for each type of specimen material as a function of the amount of compressive force applied. Ultrasonic wave velocity is affected primarily by the deformation of the material, and therefore simultaneous measurement is required. Amplitude of the ultrasonic wave, and therefore measurements of wave attenuation, is affected primarily by the amount of contact, which is dependent upon the applied compression. While the compression does tend to deform the materials such as prepreg slightly, the deformation is uniform, constant, and readily measured by a deformation gauge optionally provided with the apparatus. Consequently, it is possible to compensate for such compression in the calculations of the ultrasonic attenuation, time of flight, or other parameters derived from the data taken.

Either one or two transducers may be used. If a single transducer is used both to introduce ultrasonic pulses into the specimen and to receive the modified pulses back from the specimen, that transducer is pressed against one flat surface uniformly during operation. If two transducers are used, one to transmit and the other to receive the ultrasonic signals, then the transducers are oriented in a facing but spaced apart relationship along an axis so that the specimen is sandwiched between the two transducers under the controlled compression force.

The apparatus can be provided both as a frame-mounted instrument most suitable for laboratory or factory operation, or as a hand-held unit suitable for field operation. In the former, the transducers are mounted in a rigid frame, with one of the transducers movable on a support rod so that specimens of various sizes can be accommodated. A dead-weight loading is preferably provided, and a displacement gauge built into the unit measures the amount of deformation of the specimen under the loading. In the portable model, a pressure gauge indicates the loading, and a separate displacement gauge is used as necessary to measure the amount of deformation of the specimen after the loading is applied. The apparatus is readily adapted for use with an automated or a robotic measurement system.

Thus, apparatus for performing ultrasonic measurements on a solid specimen comprises an ultrasonic transducer adapted for contacting to the surface of the specimen; a compression loader for forcing the ultrasonic transducer against the surface of the specimen with a reproducibly controllable constant force; and a controller that receives a signal from the transducer. This apparatus can be stationary or portable, and can optionally utilize a second transducer for transmission measurements. The apparatus preferably includes displacement measuring means for determining the location of the transducer or transducers.

In one preferred embodiment, apparatus for performing ultrasonic measurements on a solid specimen comprises a pair of ultrasonic transducers disposed in a facing but spaced apart relationship to each other along a vertical axis, so that a specimen may be placed between the ultrasonic transducers; a frame which supports the two ultrasonic transducers, the frame including a support rod movable in the vertical direction within the frame and to which one of the transducers is fixed, so that the transducer is movable along the vertical axis and is forced toward the other of the transducers under the dead loading weight of the support rod, thereby compressing the specimen between the transducers under a constant, reproducible force; a displacement gauge that measures the relative position along the vertical axis of the support rod with respect to the frame; and a controller that drives one of the transducers and receives a signal from the other of the transducers. This model, using two transducers, requires access to both sides of the specimen. If only one side of the specimen is accessible, as with a part bonded into a larger structure in field service, then only a single transducer is used. However, data on specimen thickness must be obtained by some other technique.

The uniform, reproducible compressive loading results in a constant degree of coupling between the transducer or transducers and the specimen, which can be duplicated for different areas of a specimen or for different specimens. The constant degree of coupling is highly significant for the accurate measuring of velocity and attenuation of the ultrasonic signal within the specimen. Variations in coupling lead to varying boundary losses as the signal is introduced into and extracted from the specimen, resulting in uncontrollable variation between tests. Applying the same pressure reduces or eliminates the variation, by causing a constant degree of coupling. The high pressure also helps to minimize coupling variations to non-metallic matrix composites by compressively reducing local surface irregularities that can sometimes appear and vary between successive tests of the same region of a specimen. Such reproducible coupling cannot be achieved by conventional coupling methods such as the application of grease between the transducer and the specimen.

The displacement gauge permits measurement of the actual thickness of the specimen as the ultrasonic measurements are taken. The two transducers are touched together along their facing surfaces when no specimen is present to establish a zero point. (When one transducer is used, it is contacted to the surface supporting the specimen to establish the zero point.) Then the specimen is inserted so that the transducers fit solidly against the opposite surfaces, and the displacement from the zero point measured. The distance between the transducers is reduced as the compressive pressure rises. This distance is the actual path traversed by the ultrasonic signal. For very thin specimens, even a small change or error in measuring the path length can be significant in making accurate measurements. For example, a typical ply of a non-metallic matrix thermoset composite prepreg is about 0.008 inches thick, so that an undetected 0.001 inch thickness variation error results in a 10% error in the measured thickness value, with a corresponding error in the computed ultrasonic velocity. The approach of the present invention avoids this source of error, resulting in more precise measurements that are reproducible.

It will now be appreciated that the present invention provides an improvement in the art of ultrasonic measurements of specimens. The apparatus ensures reproducibility by coupling the ultrasonic signals to the specimen under a controllable compressive loading. The actual path length of travel of the ultrasonic wave is measured accurately, and is divided by the propagation time to determine ultrasonic velocity. Other features and advantages of the invention will be apparent from the following more detailed description, taken in conjunction with the accompanying drawings, which illustrate, by way of example, the principles of the invention.

DETAILED DESCRIPTION OF THE PREFERRED EMBODIMENT

Figure 1:
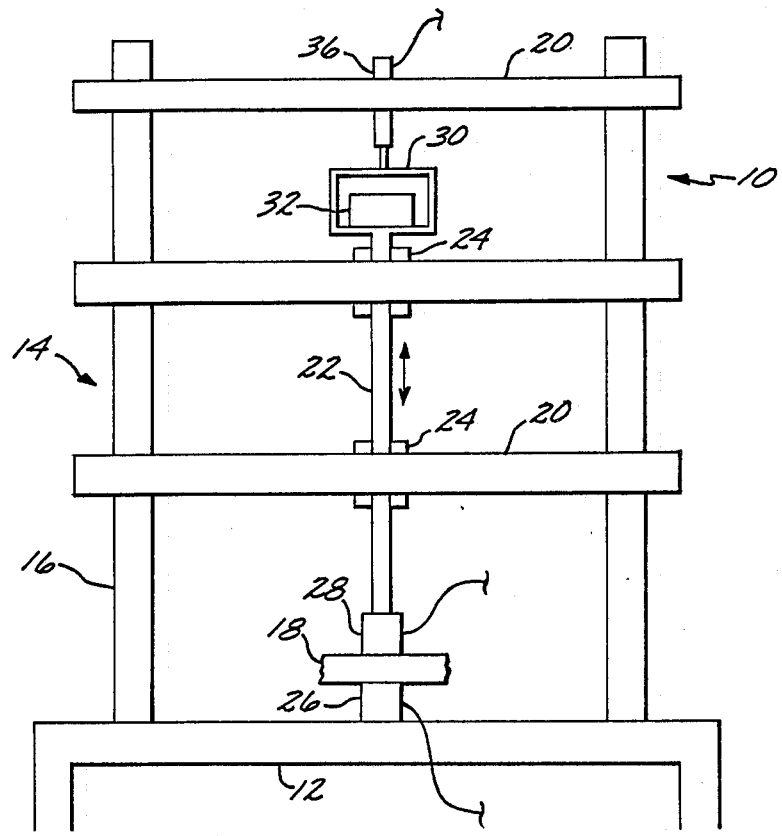
FIG. 1 is a side elevational view of a preferred apparatus.

Ultrasonic measurements are useful in determining many of the physical and structural properties of materials through which they are propagated. As an example, the velocity of an ultrasonic wave is the distance it travels through the material, the sonic path, divided by the time of travel. The velocity of the wave is dependent upon the density and viscoelastic moduli of the material, which in turn depend upon structure, so that information about the structure of the material can be gained by measuring the distance the wave travels and the time required for its propagation. Studies of different types and frequencies of ultrasonic waves propagated through solids, and changes in the waves (such as attenuation) as they travel through the solid, yield even more information.

Ultrasonic wave propagation studies are of particular interest because they can be performed in a factory or service environment with relatively compact equipment. Ultrasonic waves also do not damage or disrupt the structures through which they pass. By contrast, most other techniques for determining internal physical properties can only be effectively utilized in limited laboratory circumstances, or permanently damage the sample material. Ultrasonic measurements have therefore become important in the nondestructive determination of material properties of industrial materials, both upon construction and after use.

Ultrasonic measurements can, in principle, determine the weight fractions and moisture contents of advanced plastics, nondestructively. An ultrasonic signal is propagated through the solid, and measurements taken from which these structural characteristics can be determined. However, no consistent method for introducing the ultrasonic signals into the specimen and for extracting the ultrasonic signals from the specimen under highly controlled conditions has as yet been found. The composite materials, in both the prepreg and cured states, are highly compliant or deformable perpendicular to the surface of the sheet, and this compliance creates difficulties in introducing and extracting signals for the following reasons.

Ultrasonic waves are generated and detected by devices termed ultrasonic transducers, which create or detect waves of frequencies above those that can be heard by the human ear. The ultrasonic signal that is produced by a transmitting transducer is excited in the transducer by an electrical signal provided to the transducer, and then must be transferred to the sample through which propagation occurs. The propagated signal is then extracted from the sample by a receiving transducer. Some transducers can function as both the transmitting and receiving transducer, so that measurements are made of ultrasonic waves that are reflected within the specimen. In other cases, one transducer transmits the ultrasonic signal into the specimen, and another receives the ultrasonic specimen from the specimen after propagation.

Both the ultrasonic signal introduced and the signal received must be transferred across the boundary of the specimen from or to the transducers. The ultrasonic signal may be significantly altered by its passage across the boundary, unless care is taken to connect or "couple" the transducers to the specimen properly. A number of techniques have been developed to permit ultrasonic coupling, but all suffer from problems when used to couple transducers to non-metallic matrix composites. Most commonly, the transducer is stuck to the surface of the specimen with grease or the like, and the grease serves to transfer the signal. This procedure is not acceptable for use with prepregs, as the residual grease interferes with subsequent bonding. It also cannot be used with final parts because the grease can interfere with use of the part. Other approaches have been tried, but have not been found satisfactory for mass testing of prepreg or cured parts, particularly when in service.

Often, the ultrasonic signal must be compared with other ultrasonic signals taken from other specimens or other regions of the same specimen, and therefore the coupling must be highly precise and reproducible. There is no known testing and coupling technique that permits a highly reproducible coupling to be accomplished, with a simultaneous measurement of the sonic path as affected by pressure applied to the transducers.

The present invention is embodied in an apparatus 10, illustrated in FIG. 1. The apparatus 10 includes a rigid base 12 and an upright frame 14 set thereupon. The frame 14 conveniently is formed of two vertical uprights 16 spaced apart by a distance that permits insertion of a specimen 18 therebetween. The frame 14 is stiffened by horizontal stiffeners 20 extending between the uprights 16. The total forces involved in the apparatus 10 are not more than a few hundred pounds at most, typically less than one hundred pounds, and as a result the frame 14 need not be constructed to withstand high forces. However, rigidity is important, and the frame 14 is therefore preferably constructed of steel.

Intermediate the uprights 16 is a vertical support rod 22 that extends parallel to the uprights 16 but is free to move vertically along its axis. The support rod 22 is preferably supported in a pair of bearings 24 mounted to two of the horizontal stiffeners 20. These bearings 24 are preferably teflon sleeves, but can be roller bearings or other type of bearing. The bearings 24 provide sideways support and stability, and at the same time permit the support rod 22 to slide upwardly and downwardly. The support rod 22 does not move great distances or at high rates, so that the bearings 24 need not be selected with such complications in mind.

A first ultrasonic transducer 26 is mounted to the base 12 with its active surface facing upwardly. A second ultrasonic transducer 28 is mounted to the bottom end of the support rod 22, with its active surface facing downwardly. The first and second transducers 26 and 28 are positioned to be in facing relationship to each other, so that ultrasonic signals emitted from one are received by the other.

The specimen 18 is positioned between the two facing transducers 26 and 28, and therefore the vertical movement of the support rod 22 must be great enough to allow specimens of differing thicknesses to be placed between the transducers. When the specimen 18 is so placed, and the support rod 22 relaxed under the force of gravity, the specimen 18 is lightly pressed between the two transducers 26 and 28.

It has been found that the compression force applied to the specimen 18 through the transducers 26 and 28 should be constant but controllable to differing levels to provide optimization of this parameter for different specimen materials and configurations. However, once that optimal point has been reached, the force should be maintained precisely constant between different measurements of that specimen, and between different measurements that are to be compared with each other.

A preferred approach to achieve this feature is to use dead-weight loading of the support rod 22, which eliminates the need for a force gauge and a means to control the force. For this purpose, a weight box 30 is attached to the support rod 22 at its upper end. The weight box 30 is a simple container into which weights 32 may be added to increase the compressive force applied to the specimen 18 through the support rod 22.

Figure 2:
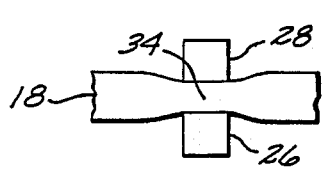
FIG. 2 is an enlarged detail of FIG. 1, illustrating the deformation of the specimen under the compressive forces.

FIG. 2 is an enlarged view of the specimen 18 and the transducers 26 and 28, with weight applied. The transducers 26 and 28 act as punches to locally reduce the thickness of the specimen 18 in a central region 34 thereof, while the remainder of the specimen 18 retains its original thickness. The ultrasonic signals pass through the central region 34, and it is important to know the local through-thickness dimension in the central region 34. As indicated earlier, the thickness of a prepreg is typically 0.008 inches, and a 0.001 inch reduction in thickness could result in a 10% error in the determination of ultrasonic velocity, if such error is undetected.

The local dimension in the central region 34 is determined using a displacement gauge 36 that measures the movement of the support rod 22. The frame 14 and support rod 22 can be considered rigid, so that any movement of the support rod 22 is due to the thickness of the specimen 18. The local thickness of the specimen 18 is determined by placing the transducers 26 and 28 face to face without the specimen 18 present, and obtaining a displacement reading from the gauge 36. The specimen 18 is then inserted between the transducers 26 and 28, and the displacement of the gauge 36 is then read again. The difference between the two readings is the local through thickness dimension of the specimen 18 in the central region 34. The through thickness dimension of the specimen 18 in the region without any applied compressive loading can be similarly determined, if that is of interest, by making the second displacement measurement as the transducer 28 first touches the upper surface of the specimen 18 when the support rod 22 is lowered.

Figure 4:
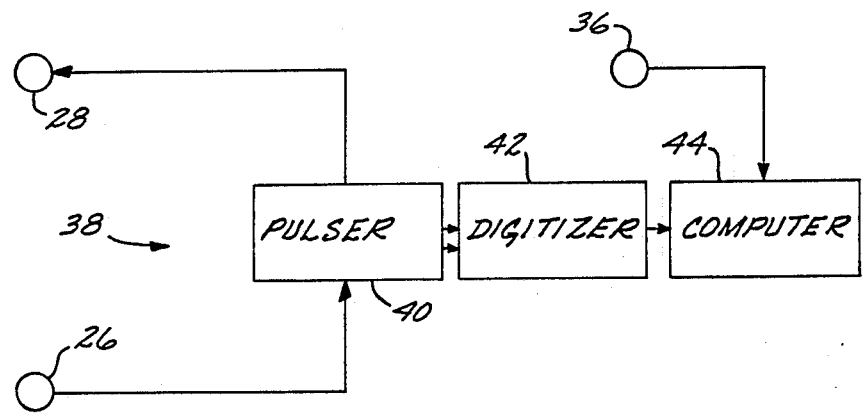
FIG. 4 is a block diagram of the control system for the apparatus.

With the transducers 26 and 28 in place and compressively forced against the specimen 18, the ultrasonic measurements can be taken under the control of a controller 38, illustrated in FIG. 4. The nature of these measurement depends upon the data required. In a preferred system, pulsed ultrasonic signals are emitted by transducer 28 under the control of a pulser 40. The pulser 40 sends a transmission pulse to the transducer 28, which transmits a corresponding signal into the specimen 18. The ultrasonic signal propagated through the specimen 18 and received by the transducer 26 is provided to the pulser 40. The waveform is digitized by a digitizer 42 and provided to a computer 44, which also receives the displacement signal from the displacement gauge 36. The information in the computer 44 can then be used to calculate the desired properties such as velocity and attenuation as necessary, that in turn characterize the material.

Ultrasonic measurements are taken using the apparatus 10 by raising the support rod 22 to separate the transducers 26 and 28, and inserting a specimen 18 into the gap between the transducers. For compliant specimens, no separate couplant is used. For rigid specimens, a drop of a completely volatile liquid couplant such as alcohol or water can be placed on the surface of each side of the specimen 18 in the region where the transducers 26 and 28 contact the specimen. The support rod 22 is lowered to permit the upper transducer 28 to rest against the specimen 18, and the measurement is taken. A manual switch may be used to indicate that a measurement is to be taken, or the controller 38 may control this function automatically. The support rod 22 is raised, and the process may be repeated with another area of the specimen 18 or another specimen. It will be appreciated that this apparatus 10 is well suited to an automated measurement operation, wherein a mechanism is provided to raise and lower the support rod 22 at the appropriate times, and wherein another mechanism translates specimens into position between the transducers.

In this preferred embodiment, the transducers 26 and 28 are Panametrics Model A109-S transducers which operate at 5 MHz, with a relatively broad band width that minimizes ringing of the transducer when used with a narrow specimen. The pulser 40 is a Panametrics Pulser Receiver Model 5052 PR. The digitizer 42 is a Tektronix Model 336 digitizing oscilloscope. The computer 44 is a Hewlett Packard Integral PC. The displacement gauge 36 is a Sylvac P25 capacitance device sensitive to 0.0001 millimeter.

Figure 3:
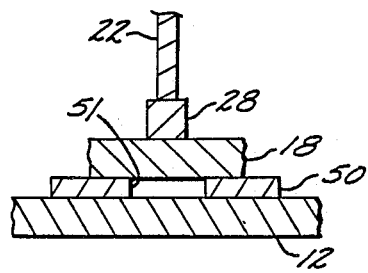
FIG. 3 is a side sectional view of a portion of FIG. 1, illustrating an alternative approach using a single transducer.

A variation of the apparatus 10 is illustrated in FIG. 3. Here the transducer 26 is omitted, and a single transducer 28 both transmits and receives the ultrasonic signal. The path length traversed by the signal is twice the local thickness of the specimen 18. The specimen 18 is supported by a support block 50, which has an aperture 51 therethrough below the specimen to provide optimal reflective properties for the reflected ultrasonic wave. This apparatus of FIG. 3 is preferred for use when only one side of the specimen is accessible.

Figure 5:
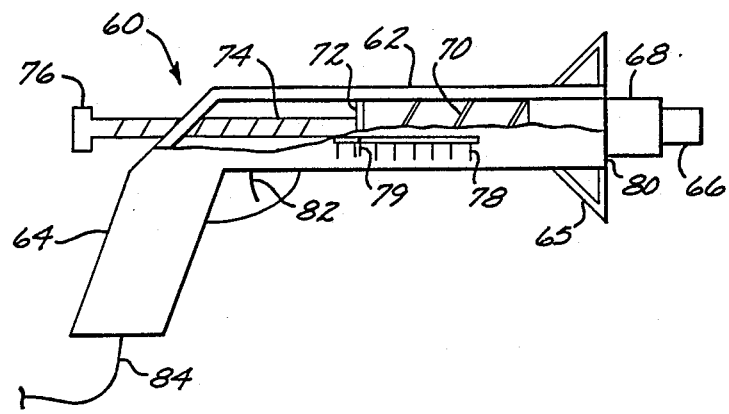
FIG. 5 is a side elevational view of a portable apparatus, with portions broken away for clarity.

FIG. 5 illustrates a preferred portable apparatus 60 which may be used in field testing of materials by ultrasonic means. The apparatus 60 is in the form of a handheld gun, having a barrel 62 and a handgrip 64 for easy manipulation. A rigid, removable skirt 65 extends outwardly from the end of the barrel 62 to steady the barrel against lateral tipping when placed against a surface of a specimen. A transducer 66 is mounted on an extendible rod 68 that extends outwardly from the end of the barrel 62. The interior end of the rod 68 is attached to a spring 70 which biases the rod 68 and the transducer 66 to extend outwardly from the barrel 62. The other end of the spring 70 is contacted by a plunger 72 supported on a threaded rod 74 that may be turned by a screw 76 on the end of the barrel 62 remote from the transducer 66, to move the plunger 72 so as to apply greater or lesser force on the end of the spring 70. A scale 78 on the outside of the barrel 62 indicates the force applied to the transducer 66 in the following manner.

Prior to a measurement, the transducer 66 extends from the end of the barrel 62. To make a measurement, the transducer 66 is pressed against the surface of the specimen to be measured, forcing the extendible rod 68 back into the barrel 62 and compressing the spring 70. When the transducer 66 is forced against the surface of the specimen so that the end 80 of the barrel 62 contacts the specimen, no further travel is possible. The spring force is measured by the position of an indicator 79 mounted to the plunger 72 in relation to the scale 78. If the spring force is other than the desired amount, the spring force is adjusted by turning the screw 76 to reach a desired force applied against the surface of the specimen through the transducer. Such adjustment is typically required for testing the first specimen of a group, but then readjustment is not required as long as the desired force is unchanged. This force is exactly and readily reproduced on successive specimens by forcing the transducer 66 down against the surface until the end 80 prevents further movement. The thickness of the specimen, if required, is measured by other means such as a separate gauge. Alternatively, the apparatus 60 could be constructed with an integral thickness gauge.

In the design illustrated in FIG. 5, spaced ultrasonic pulses are continuously transmitted to the specimen 18. The received pulse is sent to the controller 38 through a line 84 only when a trigger 82 is depressed to indicate that the proper force level is reached.

The portable apparatus may be used to collect ultrasonic data in a laboratory or factory environment, but is also operable in a service environment. That is, if a composite material is built into a structure such as an aircraft, the portable apparatus may be taken to the aircraft and contacted to the composite piece to quickly and accurately determine the ultrasonic parameters. The measurement is taken by forcing the transducer 66 against the surface of the composite piece until the end 80 of the barrel 62 touches the surface, adjusting the screw 76 until the proper force level is indicated on the scale 78, and depressing the trigger 82. The measurement is recorded in the controller, and the next area may be measured.

The apparatus and procedure of the invention thus permit reproducible ultrasonic measurements of a variety of physical parameters of a specimen material, including compliant specimens such as non-metallic matrix composites. Although a particular embodiment of the invention has been described in detail for purposes of illustration, various modifications may be made without departing from the spirit and scope of the invention. Accordingly, the invention is not to be limited except as by the appended claims.

What is claimed is:

1. Apparatus for performing ultrasonic measurements on a solid specimen, comprising:
    measurement means for introducing a first ultrasonic signal into a specimen at a first location and for receiving a second ultrasonic signal from the specimen at a second location;
    means for determining the local thickness of the specimen in a region between the first location and the second location;
    compression means for forcing said measurement means against the surface of the specimen with a reproducibly controllable constant compressive force that remains constant as said measurement means moves in response to deformation of the specimen, so that the same compressive force may be applied during the entire course of a single measurement and on successive measurements, wherein said compression means includes
        a frame for supporting said measurement means in contact with the surface of the specimen, and
        loading means for applying a dead-weight load to said measurement means to force it against the surface of the specimen; and
    control means for controlling said measurement means.

2. Apparatus for performing ultrasonic measurements on a solid specimen, comprising:
    a movable ultrasonic transducer adapted for contacting to the surface of the specimen;
    a compression loader for forcing said ultrasonic transducer against the surface of the specimen by a dead-weight load;
    locating means for measuring the position of said transducer parallel to the direction of application of the compressive force during operation of the transducer; and
    a controller that receives a signal from said transducer.

* * * * *